US009139460B2

United States Patent
Hong (10) Patent No.: US 9,139,460 B2
(45) Date of Patent: Sep. 22, 2015

(54) METHODS FOR DEACTIVATING BIOMASS

(75) Inventor: P. K. Andy Hong, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 338 days.

(21) Appl. No.: 13/636,639

(22) PCT Filed: Mar. 23, 2011

(86) PCT No.: PCT/US2011/029653
§ 371 (c)(1),
(2), (4) Date: Dec. 21, 2012

(87) PCT Pub. No.: WO2011/119753
PCT Pub. Date: Sep. 29, 2011

(65) Prior Publication Data
US 2013/0192138 A1    Aug. 1, 2013

Related U.S. Application Data (60) Provisional application No. 61/316,511, filed on Mar. 23, 2010.

(51) Int. Cl.
C02F 11/06 (2006.01)
C02F 1/34 (2006.01)
(Continued)

(52) U.S. Cl.
CPC . C02F 11/06 (2013.01); C10L 3/08 (2013.01); C10L 5/44 (2013.01); C10L 5/46 (2013.01); C12M 47/06 (2013.01); C12N 1/066 (2013.01); *C02F 1/34* (2013.01); *C02F 1/36* (2013.01); *C02F 1/722* (2013.01); *C02F 1/76* (2013.01); *C02F 1/78* (2013.01); *C02F 2301/066* (2013.01);
(Continued)

(58) Field of Classification Search
CPC ............... C02F 1/20; C02F 1/34; C02F 1/36; C02F 1/722; C02F 1/76; C02F 1/78; C02F 2303/06; C02F 11/06; C10L 3/08; C10L 5/44; C10L 5/46; C12M 47/06; C12N 1/066; Y02E 50/10; Y02E 50/30; Y02E 50/343; B08B 3/10
See application file for complete search history.

(56) References Cited

U.S. PATENT DOCUMENTS

| | | | |
|---|---|---|---|
| 5,378,366 A * | 1/1995 | Yen | 210/667 |
| 5,865,898 A | 2/1999 | Holtzapple et al. | |
| 6,200,486 B1 * | 3/2001 | Chahine et al. | 210/748.03 |
| 7,527,734 B1 | 5/2009 | Shepherd | |
| 2006/0096163 A1 | 5/2006 | Dickinson et al. | |
| 2009/0159536 A1 | 6/2009 | Hong | |

(Continued)

FOREIGN PATENT DOCUMENTS

| | | |
|---|---|---|
| CN | 101693841 | 11/2009 |
| CN | 101870643 | 10/2010 |

(Continued)

*Primary Examiner* — Lucas Stelling
(74) *Attorney, Agent, or Firm* — Thorpe North & Western, LLP (57) ABSTRACT

A method of deactivating biomass is set forth. The method includes two stages, a disrupting stage and a rupture stage. The disrupting stage includes the steps of injecting an oxidizer gas into the biomass with minimal or significant elevated pressure and then a depressurizing of the biomass. The steps cause a disruption of cellular membranes of cells present in the biomass. The rupture stage includes the step of injecting the biomass with a rupture gas sufficient to pressurize the biomass to a second elevated pressure following by the depressurizing of the biomass. The injecting and depressurizing steps of the rupture stage can be repeated at least two times in order to rupture the cell membranes and expose residual cell contents.

24 Claims, 4 Drawing Sheets

(51) Int. Cl.
  *C02F 1/36*      (2006.01)
  *C02F 1/72*      (2006.01)
  *C10L 5/44*      (2006.01)
  *C10L 5/46*      (2006.01)
  *C12N 1/06*      (2006.01)
  *C10L 3/08*      (2006.01)
  *C12M 1/00*      (2006.01)
  *C02F 1/76*      (2006.01)
  *C02F 1/78*      (2006.01)

(52) U.S. Cl.
  CPC ............. *C02F 2303/06* (2013.01); *Y02E 50/10* (2013.01); *Y02E 50/30* (2013.01); *Y02E 50/343* (2013.01)

(56) References Cited

U.S. PATENT DOCUMENTS

2010/0139265 A1    6/2010  Stroiazzo
2010/0224835 A1    9/2010  Chornet et al.

FOREIGN PATENT DOCUMENTS

| | | |
|---|---|---|
| JP | 59/105897 | 6/1984 |
| KR | 1002699 | 7/1997 |
| SU | 2076361 | 4/1992 |
| WO | WO 2007120735 A2 * | 10/2007 |
| WO | WO 2009/068875 | 6/2009 |
| WO | WO 2010/123141 | 10/2010 |

* cited by examiner

| | Compression equilibrium time | Vent Time (s) | TS | TSS | TDS | VDS | VSS | TDS/TSS | VDS/TSS | (TSS+TDS)/TS | TS/TS0 | TDS-VDS | %Inc | tCOD | sCOD | BOD | BOD/tCOD | sCOD/tCOD | pH |
|---|---|---|---|---|---|---|---|---|---|---|---|---|---|---|---|---|---|---|---|
| | | | | | | | | | | MLSS | | | | | | | | | |
| None[a] | - | - | 3998 ±346 | 2919 ±339 | 785 ±224 | 257 ±109 | 2389 ±294 | 0.27 | 0.09 | 0.93 | 1.00 | 528 | - | 4905 ±920 | 36 ±8 | 150 ±25 | 0.031 | 0.007 | 6.7 ±0.4 |
| 1+9 1035 kPa[b] | 30, 30 | 150 | 3616 ±260 | 2468 ±71 | 1059 ±47 | 371 ±41 | 1988 ±62 | 0.43 | 0.15 | 0.98 | 0.90 | 688 | 0.30 | 3900 ±354 | 142 ±27 | 132 ±41 | 0.034 | 0.036 | 6.3 ±0.4 |
| 3+7 345 kPa[b] | 5, 55 | 40 | 2530 ±201 | 1264 ±113 | 908 ±88 | 356 ±6 | 1028 ±102 | 0.72 | 0.28 | 0.86 | 0.63 | 552 | 0.05 | 3385 ±318 | 158 ±16 | 177 ±16 | 0.052 | 0.047 | 7.0 ±0.0 |
| 3+7 690 kPa[b] | 15, 45 | 60 | 2872 ±34 | 1476 ±112 | 962 ±122 | 343 ±81 | 1196 ±43 | 0.65 | 0.23 | 0.85 | 0.72 | 619 | 0.17 | 2905 ±226 | 353 ±2 | 158 ±3 | 0.054 | 0.122 | 6.6 ±0.6 |
| 3+7 1035 kPa[b] | 30, 30 | 150 | 3070 ±260 | 1290 ±71 | 1376 ±47 | 697 ±27 | 993 ±74 | 1.07 | 0.54 | 0.87 | 0.77 | 679 | 0.29 | 3658 ±1248 | 600±57 | 342 ±40 | 0.094 | 0.164 | 6.5 ±0.2 |
| | | | | | | | | | | RAS | | | | | | | | | |
| None[b] | - | - | 9696 ±979 | 7928 ±1048 | 779 ±18 | 119 ±4 | 6436 ±853 | 0.10 | 0.02 | 0.90 | 1.00 | 660 | - | 13494 ±765 | 115 ±44 | N.A. | N.A. | 0.009 | 7.4 ±0.0 |
| 3+7 1035 KpA[b] | 30, 30 | 150 | 8476 ±503 | 5618 ±52 | 2397 ±262 | 1448 ±59 | 4460 ±13 | 0.43 | 0.26 | 0.95 | 0.87 | 949 | 0.44 | 9764 ±211 | 1925 ±38 | N.A. | N.A. | 0.197 | 6.1 ±0.7 |

[a]Solids analysis was replicated 7 times, BOD$_5$ measurement was replicated 4 times.
[d]Duplicates
[c]N.A.: Data not available

METHODS FOR DEACTIVATING BIOMASS

RELATED APPLICATIONS

This application is a U.S. national stage entry of PCT International Application No. PCT/US11/29653, filed Mar. 23, 2011, which claims priority to U.S. Provisional Application No. 61/316,511, filed Mar. 23, 2010.

FIELD OF THE INVENTION

The present invention is drawn to methods of deactivating biomass. More specifically, the invention relates to processes and methods using pressurizing-depressurizing treatment for biomass.

BACKGROUND

The activated sludge process was discovered in 1913. Experiments on treating sewage in a draw-and-fill reactor (the precursor to today's sequencing batch reactor) produced a highly treated effluent. Believing that the sludge had been activated (in a similar manner to activated carbon) the process was named activated sludge. Not until much later was it realized that what had actually occurred was a means to concentrate biological organisms, decoupling the liquid retention time (ideally, low, for a compact treatment system) from the solids retention time (ideally, fairly high, for an effluent low in $BOD_5$ and ammonia.) In a sewage (or industrial wastewater) treatment plant, the activated sludge process can be used for one or several of the following purposes including oxidizing carbonaceous matter: biological matter, oxidizing nitrogeneous matter such as ammonium and nitrogen in biological materials, removing phosphate, driving off entrained gases carbon dioxide, ammonia, nitrogen, etc, generating a biological floc, and generating a liquor low in dissolved or suspended material. Regardless of the reason for making the activated sludge, once the intended use is achieved, there remains a need to deactivate and dispose of the activated sludge in an efficient and cost effective manner. Accordingly, research continues in an effort to develop methods for accomplishing the deactivation and disposal of the sludge.

SUMMARY

A method of deactivating biomass is disclosed and described. The method includes two stages, a disrupting stage and a rupture stage. The disrupting stage includes the steps of injecting an oxidizing agent so as to cause a disruption of cellular membranes of cells present in the biomass. Optionally, the disrupting state can include pressurizing the biomass to an elevated pressure and then depressurizing of the biomass. The rupture stage includes the step of injecting the biomass with a rupture gas sufficient to pressurize the biomass to a second elevated pressure following by the depressurizing of the biomass. The injecting and depressurizing steps of the rupture stage can be executed at least two times in order to rupture the cell membranes and expose residual cell contents.

A greater understanding of these methods may be had from reference to the following detailed description and the appended claims.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In describing and claiming the present invention, the following terminology will be used in accordance with the definitions set forth below.

It is noted that, as used herein, the singular forms of "a," "an," and "the" include plural referents unless the context clearly dictates otherwise. Thus, for example, reference to "a microorganism" includes one or more of such contaminants, reference to "a rupture fluid" includes reference to one or more expansion fluids, and reference to "injecting" includes reference to one or more of such steps.

DEFINITIONS

As used herein the term, "air" means and refers to a gaseous mixture that comprises at least about 20 mole percent $O_2$.

The term "oxidizer gas" includes any gaseous chemical compound or group of compounds which alone or collectively can oxidize and act to disrupt the cellular membranes of an organism. Examples of oxidizer gases which can be used in the present invention include but are not limited to ozone, chlorine gas, and mixtures thereof.

The term "activated sludge" is intended to take on the term as used in the art, namely sewage and/or industrial wastewaters (collectively sludge) that has had oxygen introduced therein and which has been combined with organisms in order to develop a biological floc which reduces the organic materials of the sludge.

As used herein, the term "cellular membrane" refers to biological membranes and structures including cell wall that separate the interior of a cell from the external environment. The cellular membranes referred to include membranes of both single-cell and multiple-cell organisms, including both prokaryotic and eukaryotic cells.

As used herein, the term "ozone" means and refers to a colorless gaseous substance ($O_3$) obtained (as by the passage of an electrical current in oxygen) as an allotropic form of oxygen, containing three atoms in the molecule. Ozone is about 1.5 times as dense as oxygen and 12.5 times more soluble in water and at high doses leaves substantially no residuals or byproducts except oxygen and a minimal amount of carbon dioxide, trace elements, and water. Ozone can be manufactured from dry air or from an oxygen containing gas by passing the gas through an electric field of high potential sufficient to generate a corona discharge between the electrodes. This corona discharge is just under the energy level of an automotive spark plug. Ultraviolet light and shorter-wavelength radiation also causes oxygen to undergo conversion to $O_3$, which may be used for industrial wastewater. Ozone is a more potent germicide than hypochlorous acid by factors of 10-100 fold and disinfects about 3125 times faster than chlorine. However, ozone is highly unstable and must typically be generated on site. The measure of an oxidizer and its ability to oxidize organic and inorganic material is its oxidation potential (measured in volts of electrical energy). The oxidation potential of $O_3$ (−2.07 V) is greater than that of hypochlorous acid (−1.49 V) or chlorine (−1.36 V), the latter agents being widely used in water treatment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

A method of deactivating biomass can include two stages, a disrupting stage and a rupture stage. The disrupting stage includes the steps of injecting an oxidizing agent into the biomass sufficient to cause a disruption of cellular membranes of cells present in the biomass. Optionally, the biomass can be pressurized to an elevated pressure and then a depressurized. The rupture stage includes the step of injecting the biomass with a rupture gas sufficient to pressurize the biomass to a second elevated pressure following by the depressurizing of the biomass. The injecting and depressurizing steps of the rupture stage can be executed at least two times in order to rupture the cell membranes and expose residual cell contents. In one embodiment, the method can further include the step of digesting the residual cell contents to form a biofuel.

Small molecules such as $O_2$, $CO_2$, and $H_2O$ can transport across cell walls and membranes. The method can accelerate the transport via a number of factors including changes of dissolved gas solubility due to changes in headspace pressure, diffusion of the dissolved gas across the membrane due to the increased concentration gradient, gas accumulation in the cells due to the repeated pressure cycles, and transport of water across the membrane and cell wall due to reverse osmosis. The dissolved concentration of the selected gas is increased by pressurization, resulting in a much higher dissolved concentration in the bulk liquid. This increased concentration is one that microorganisms have rarely encountered and creates a concentration gradient the microbes are ill equipped to defend. The concentration gradient across the cell membrane drives dissolved gas into the cell, increasing the dissolved gas concentration within the cell. When the pressure is rapidly reduced, gas formation and expansion occur within the cell, causing the formation of gas pockets in the cell (as transport across the membrane is slower than decompression). Gas accumulation in the cells during repeated pressure cycles leads to eventual rupture of the cells. When gas pockets appear in cells, water can transport via reverse osmosis across the cell membrane during compression, carrying high concentration of dissolved gas with it into the cells. This leads to even more rapid gas accumulation and expansion within the cell and thus further accelerates the rupture process in subsequent pressure cycles.

It has been discovered that repeated pressure cycles reaching 100 psi during compression can be sufficient to rupture activated sludge. Cell membrane/wall may exhibit elasticity (expansion and contraction) to deal with the pressure cycles. In some embodiments, ozone can be used in the initial cycles to oxidize and disrupt the membrane, leading to rupture during subsequent cycles.

The methods provide increased benefits in that they 1) process a large volume of activated sludge at once directly from secondary clarifier underflow; 2) process any solid concentrations from low to very high (e.g., <3,000 mg/L to 100,000 mg/L); 3) are not be susceptible to interference or blockage by debris causing equipment maintenance issues; 4) require much less energy to pressurize the small headspace, as compared to other more energy demanding techniques. Other advantages include that there is no need for addition of acid or caustic, the method can be effective at room temperature in a matter of minutes. One embodiment of a system that can be utilized to achieve desired results can be found in FIG. 2. Though the process is batch-based, several units can be operated in parallel to handle continuous processing needs.

Figure 2:
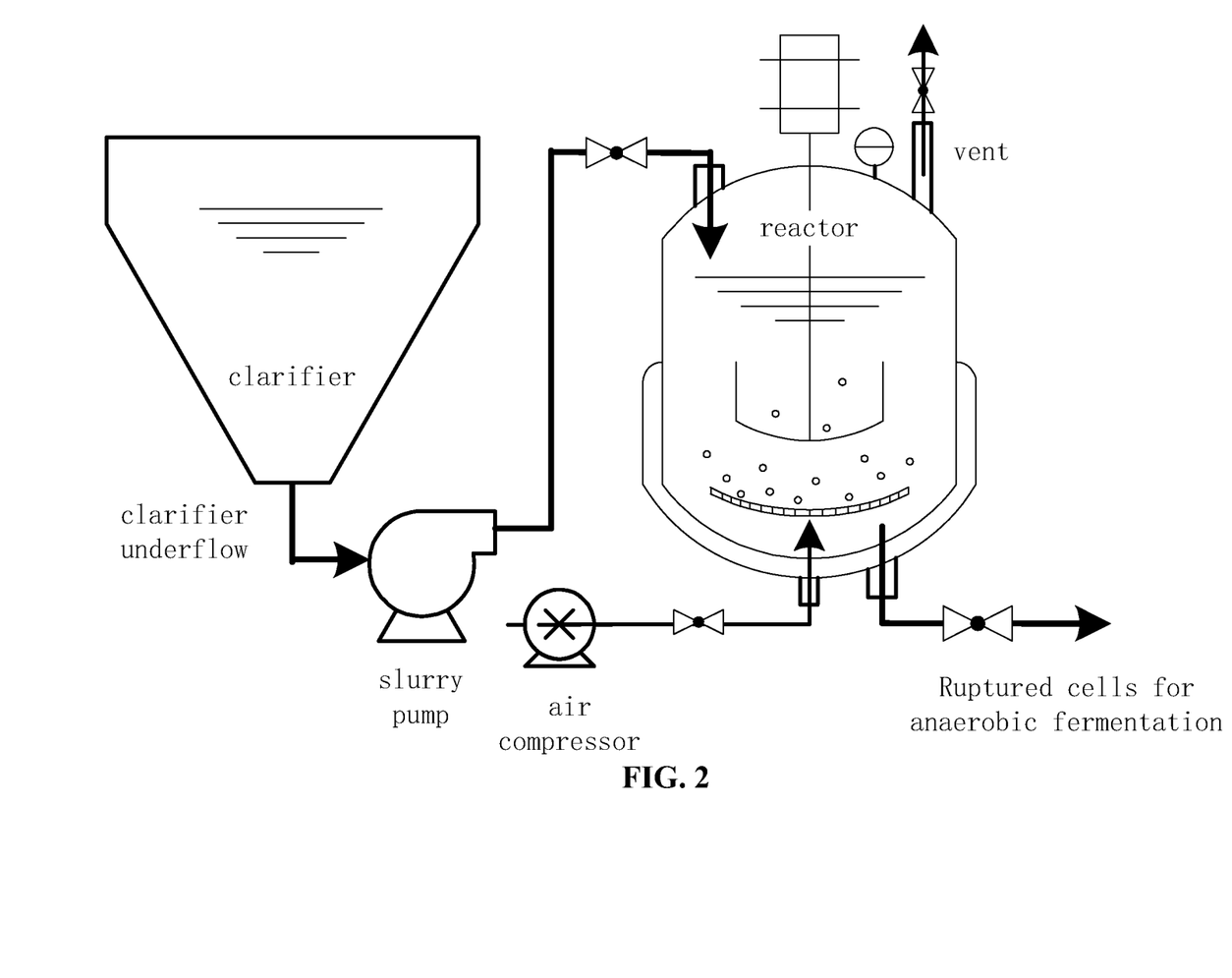
FIG. 2 shows one embodiment of a reactor and application of the technology in activated sludge deactivation/solubilization.

In one embodiment, operation of a reactor for solubilization of activated sludge, such as in a system shown in FIG. 2, can follow the general steps of 1) intake, 2) injection 3) compression, 4) decompression, 5) repetition of compression/decompression steps, and 6) discharge of the treated sludge from the treatment vessel. In greater detail, in one embodiment, the reactor takes clarifier underflow containing activated sludge (e.g., 12,000 mg/L or higher) from a pump and fills to about 80% volume (i.e., 20% remaining headspace). Following intake of the activated sludge, an air compressor can sparge an oxidizer gas into the reactor with stirring. The injection of the oxidizer gas can be independent or in conjunction with an increase in the pressure within the vessel, specifically to a headspace pressure of ambient to 300 psi. Ambient can be used when injecting oxidizing gas without pressurizing during the disrupting stage. Once compression pressure (e.g., 100 psi) is reached in the headspace, the pressure can be released via venting at the reactor top. In some embodiments, it can be desirable to allow for a short period of equilibration prior to venting or releasing the pressure. The equilibration period can be about 10 seconds to about 600 seconds. Additional injection, compression, and decompression cycles can be performed using a rupture gas in order to cause rupture of the cells. The number of cycles can vary but can depend on the nature of the activated sludge or biomass, temperature, and other factors. However, as a general guideline the number of cycles can range from 3 to 50 times, and in one aspect from 5 to 10 times although a greater number of cycles may be desired for some applications. Cycles can be repeated sufficiently to provide rupturing of at least 60%, in some cases 90% and in many cases substantially all of the cells present in the activated sludge. Once the prescribed number of pressure cycles is completed. The treated activated sludge can be released by pressure ejection to the next stage of fermentation or conversion for bioenergy/biofuel.

Activated sludge deactivation can be characterized according to operation conditions such as pressure (50-150 psi), pressure cycles (5-10), ozone concentration (0-3%), compression and decompression speeds (3-30 s), and sludge concentration (3,000-15,000 mg/L). BOD and soluble COD before and after solubilization can be quantified. Enhanced batch, anaerobic gas production (methane) following solubilization can also be quantified by GC/FID. The biomass in the activated sludge can be any suitable material having cell walls and/or membranes. Non-limiting examples of biomass can include activated sludge, algae, and the like. In one aspect, the biomass is activated sludge. In another aspect, the biomass can be algae such that the biofuel is an algae-derived biofuel. Blue-green algae (algal bloom) which appears in nutrient-rich water (e.g., improperly treated or untreated sewage discharge to a water body) can be effectively treated.

Depending on the particular characteristics of the biomass being deactivated, it can be desirable to repeat the disrupting stage multiple times. In one embodiment, the disrupting stage can be repeated 1-10 times. In another embodiment, the disrupting stage can be repeated 2 to 4 times. Similarly, the rupturing step can be repeated at least once and up to 100 times or more. In one embodiment, the rupturing step can be repeated 4 to 15 times. In an additional embodiment, the rupturing step can be repeated 6 to 10 times. As a guideline, optimal time duration and number of pressurization cycles can be readily determined for each disrupting and rupturing fluid based on monitoring and/or testing. For example, two disrupting cycles may be sufficient when only a small dose of oxidant is needed to disrupt the membrane in the disrupting stage, and a higher pressure in the rupture stage can reduce the needed number of pressure cycles in the rupturing stage.

The duration of each of the pressurizing and depressurizing steps can be varied based on a number of factors including, but not limited to, the exact nature or quantity of the biomass, the type and amount of oxidizing agent injected, the change in pressure during each of the pressurization or depressurization steps, and the like. The pressurizing and depressurizing steps can have a time duration varying from seconds to minutes for the individual steps depending on the particular system of biomass and disrupting and rupturing fluids. In one embodiment, each of the duration of the repetitions of the disrupting stage and/or the rupturing stage can have a duration of 20 seconds to 20 minutes for each complete cycle. In another embodiment, the duration of each cycle or repetition of the disrupting stage and/or the rupturing stage can have a duration of duration of 25 seconds to 10 minutes. In yet another embodiment, the duration of each cycle or repetition of the disrupting stage and/or the rupturing stage can have a duration of duration of 30 seconds to 3 minutes. In yet another embodiment, the duration of each cycle repetition of the disrupting stage and/or the rupturing stage can have a duration of 30 seconds to 2 minutes.

In one embodiment, the injecting and depressurizing steps of the rupture phase of the method can have a collective duration period of about 20 seconds to about 2 minutes. In another embodiment, the injecting and depressurizing steps can have a collective duration of about 25 seconds to about 90 seconds. In some embodiments, an additional equilibrating period or step can be inserted between injecting step and the depressurizing step of the rupture phase of the method. When present equilibrating period can have a duration of 5 seconds to 2 minutes. In one embodiment, the equilibrating period can have a duration of 7 seconds to 1 minute. When present, the equilibrium period can be added to the duration of the collective duration of the injecting and depressurizing steps.

The elevated pressure of each of the first elevated pressure can be 0-30 psi and the second elevated pressure can be at least about 30 psi. The elevated pressures, both first and second, can be pressures that are about 30 psi to about 1000 psi higher than the initial pressure of the biomass. In one embodiment, each of the first elevated pressure and second elevated pressure can be about 80 psi to about 200 psi. In another embodiment, the first elevated pressure and the second elevated pressure can be different.

The depressurizing steps in both the disrupting and the rupturing stages can result in pressure reductions of from about 30 psi to about 1000 psi. In one embodiment, the depressurizing step can result in pressure reductions of the sample of from 40 psi to about 200 psi. In one embodiment, depressurization step results in a pressure reduction of from 100 to 500 psi. In another embodiment, the pressure differential during the depressurization step results in a pressure reduction of at least 50 psi. In yet a further embodiment the pressure reduction during the depressurization step leaves the now sludge at ambient pressure.

The oxidizing agent used in the disruption stage acts to disrupt the membrane of the cells, e.g. bacteria, present in the biomass. Without being limited by any particular theory, it is speculated that the oxidizing agent disrupts the membrane of the cells thereby reducing the flexibility of the cells or the membrane's ability to regulate material flow across it. The reduced flexibility or fouled permeability of the cell facilitates the cells rupturing during the rupture stage. Generally, the oxidizing agent can be a gas, liquid or solid. Expandable oxidizing agents can be used in conjunction with pressure cycling as discussed, although non-expandable agents can also be used with pressure cycling if desired. Non-limiting examples of solid and liquid chemical oxidants can include $KMnO_4$, $K_2FeO_4$, NaClO, chlorine in a liquid form, and the like. In another aspect, the oxidizing agent can be any suitable oxidizer gas known in the art. Non-limiting examples of oxidizer gases that can be used include ozone, chlorine gas, fluorine gas, nitrogen oxide, and mixtures thereof. In one embodiment, the oxidizer gas can include ozone.

The rupture gas injected during the rupture stage, injected in at least two cycles, acts to swell and rupture the cells in the biomass, thereby deactivating (or solubilizing) the sludge. The rupture gas used in the rupture stage can be any gas, different than the oxidizer gas, which can cause the cells to rupture. Non-limiting examples of rupture gases can include air, carbon dioxide, nitrogen, argon, helium, oxygen, and mixtures thereof. It is important to note that a second oxidizer gas, or a different concentration of the same oxidizer gas can be used during the rupture stage as the rupture gas.

In some cases, the disrupting and rupturing occur sequentially. However, disrupting and rupturing can occur seamlessly (e.g. without pause) or concurrently. Furthermore, these two stages can be brought about with or without operation changes throughout inactivation. For example, in the former, ozone may be used only in the initial pressure cycles but not used in the later cycles (i.e., with operation changes). In the latter, a liquid or solid oxidant can be initially added, and then pressure cycles are applied till inactivation completion (i.e., with no operation changes throughout).

Typically, the methods can be performed at ambient temperatures (e.g. not accounting for temperature fluctuations as a result of pressure changes), although other temperatures may also be useful.

In an embodiment, the method can be accomplished in a reactor. In various reactors, vents, inlets, outlets and the like may be arranged about the reactor as needed for the application. Further, various reactors can work as a batch or as a flow reactor with respect to the biomass. In one embodiment, the method can take place in a reactor that has an occupied volume, i.e. volume occupied by biomass, to headspace volume (unoccupied volume within the reactor) ratio of 1:9 to about 9:1.

In an embodiment, the process for the deactivating the sludge can be further aided by some form of agitation during at least one of the steps of injecting, or depressurizing of both the disrupting stage and the rupture stage. Examples of agitation mechanisms include, but are not limited to stirring, shaking, ultrasound, and the like. It is noted multiple agitation mechanisms can be combined during any given step of contaminant removal.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description or following examples. All changes which come within the meaning and range of equivalency of the claims are to be embraced within their scope.

EXAMPLES

Example 1

Method for Deactivating Activated Sludge

Figure 1A:
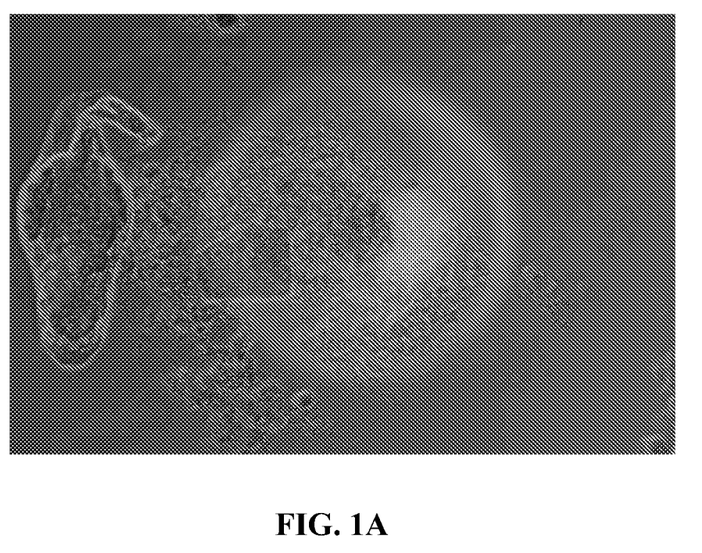
FIGS. 1A and 1B are microscope images showing sludge deactivation/solubilization in samples.
Figure 1B:
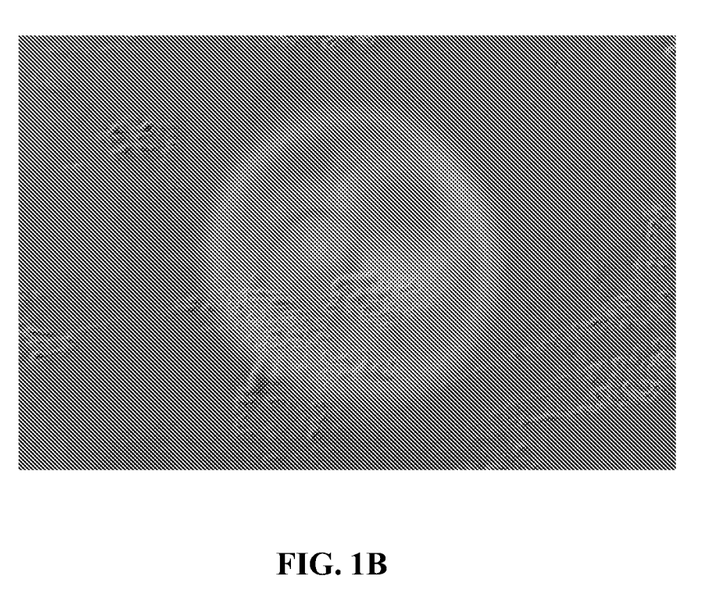

The method can involve repeated pressure cycles each consisting of a compression stage and a venting stage. In one embodiment, the compression stage can be 100-150 psi in the headspace of a closed vessel by use of a compressor, saturating the aqueous activated sludge suspension with dissolved air. The venting stage can result in rapid pressure drops, e.g. to ambient pressure, and can produce rapidly expanding gas bubbles within the microorganism's cell wall (due to escape of oversaturated dissolved gas). Repeated pressure cycles can result in increasing transport of dissolved gas into cell and gas expansion from within, thereby leading to rupture of the cell wall (i.e. air embolism of the activated sludge). Activated sludge before treatment and after 3 ozone and 7 air cycles showed a distinct decrease in visible debris within the samples with the treated sample being nearly clear while the initial untreated sample was highly cloudy. FIG. 1A shows fresh activated sludge at 400× magnification with flocs and microorganism (rotifer) present. FIG. 1B shows activated sludge at 800× magnification after 3 ozone and 7 air cycles (150 psi) with only gluey substances and no microorganisms or flocs observed.

Example 2

System and Methodology for Deactivating Activated Sludge

A reactor system, such as shown in FIG. 2, can be used to deactivate activated sludge in accordance with the methods of the present invention.

The operation of the reactor for solubilization of activated sludge can be as described below.

The reactor takes clarifier underflow containing activated sludge (e.g., 6,000 mg/L or higher) from a slurry pump and fills to about 80% volume (i.e., 20% remaining headspace).

An air compressor sparges air (or other gases such as $CO_2$ as determined effective) into the reactor with stirring and pressurizes the headspace to 100 psi.

Once compression pressure (e.g., 100 psi) is reached in the headspace, the pressure is released via venting at the reactor top.

The pressure cycle consisting of compression and decompression is repeated to a prescribed number of times for solubilization of sludge (e.g., 5 to 10 times as determined to be adequate).

Once the prescribed number of pressure cycles is completed. The treated activated sludge is released by pressure ejection to the next stage of fermentation for bioenergy.

Cell membranes typically allow small molecules such as $O_2$, $CO_2$, and $H_2O$ to transport pass through or be transported across. The methods can work to deactivate activated sludge as described below:

Changes of Dissolved Gas Solubility Due to Changes in Headspace Pressure.

The dissolved concentration of the selected gas is increased by pressurization, resulting in a much higher dissolved concentration in the bulk liquid that the microorganisms have rarely encountered, against such concentration gradient the microbes are ill equipped to defend.

The concentration gradient across the cell membrane drives dissolved gas into the cell, increasing the dissolved gas concentration within the cell. When the pressure is rapidly reduced, gas formation and expansion occur within the cell, causing the formation of gas pockets in the cell (as transport across the membrane is slower than decompression). Gas accumulation in the cells during repeated pressure cycles leads to eventual rupture of the cells.

When gas pockets appear in cells, water can transport via reverse osmosis across the cell membrane during compression, carrying high concentration of dissolved gas with it into the cells. This leads to even more rapid gas accumulation and expansion within the cell and thus further accelerates the rupture process in subsequent pressure cycles. It is anticipated that repeated pressure cycles reaching 100 psi during compression can be used to rupture cells present in the activated sludge. It may be possible that increasing compression pressure may reduce the number of pressure cycles and/or process time to rupture cells. Practicable pressures can be determined by adjusting and fine-tuning the process along with other process parameters.

This technology is advantageous relative to nozzle, as it is capable of processing a large volume of activated sludge at once directly from secondary clarifier underflow. Further the methods are capable of processing any solid concentrations from low to very high (e.g., <3,000 mg/L to 100,000 mg/L). These processes are also not susceptible to interference or blockage by debris causing equipment maintenance issues. Much less energy is needed to pressurize the small headspace, relative to more energy required to power the liquid and contents through nozzles. Additionally, the process is advantageous because it can be configured as a continuous or batch process. When the process is batch-based, several reactors or chambers can be operated in parallel in order to handle continuous processing needs. For example, ten pressure cycles can be completed within 10 min with ease, which will process large batches alike. The process time can depend on several operation parameters such as compression and decompression rates (which affect degrees of saturation), air compressor capacity, headspace volume of the reactor, etc.

Example 3

Collection and Treatment of Activated Sludge by Repeated Pressurization Cycles

Two activated sludge samples, mixed liquor suspended solids (MLSS) and recycled activated sludge (RAS), were collected on a weekly basis from the Central Valley Water Reclamation Facility (CVWRF) in Salt Lake City, Utah. The samples were maintained in 4-L bottles at room temperature and fed with 1 g of glucose per day with continual aeration. The total chemical oxygen demand (tCOD) and soluble COD (sCOD) of the activated sludge (AS) were tested with a HACH COD test kit before and after filtration through a glass filter of 1.2 µm. In order to accelerate filtration of the activated sludge, the samples were first centrifuged at 1000×g at 20° C. for 15 minutes. Various measures were taken including the five-day dissolved solids (TDS), the volatile suspended solids (VSS), and the volatile dissolved solids (VDS). Each was determined using Standard Methods.

The activated sludge samples were treated by 3 pressure cycles of ozonation and 7 additional cycles of aeration or by both pressure cycles of ozonation through using pressure of 1035 kPa, or as specified. The DNA fragments, from both before and after treatment, were analyzed using DNA electrophoresis, which was performed at 150 V for about 30 min. Duplicate DNA and protein concentrations in the treated RAS were determined using diphenylamine reactions and modified Bradford protein assay, respectively. The treated samples (1.0 mL) were placed in screw-capped tubes along with 1.0 mL of 20% (wt/vol) perchloric acid. For DNA concentration determination testing, two mL of glacial acetic acid containing 4% (wt/vol) diphenylamine and 0.2 mL 0.16% (wt/vol) acetaldehyde solution were added to the tubes. The tubes were then gently agitated and incubated overnight at 30° C. Absorbance values for the samples and a salmon sperm DNA standard (5-50 µg/m Sigma Aldrich) were measured at wavelengths of 595 nm and 700 nm with a spectrophotometer). The DNA concentrations for the samples was determined using a calibration curve prepared using the DNA standards. The protein standard used in the protein testing was bovine serum albumin (0.2 to 1.5 mg/ml). Each of the samples (500 µL), or standards (100 µL), was added into a clean test tube with 5.0 mL diluted reagent (1 part dye reagent with 4 parts distilled-deionized water). The tubes were incubated at room temperature for 5 minutes and were measured for absorbance at 595 nm.

The pressure-assisted ozonation testing was accomplished by placing a volume of MLSS or RAS in a closed reactor (such as one as described in Example 2) and performing compression and decompression cycles. The reactor can include a magnetically coupled stirrer, a pressure gauge, a gas vent (such as at the top of the reactor), and a gas injector. The ozone concentrations of the gas used was 3% before compression and 0.06% (V/V) after compression. The compression of the samples began with the injection of either the ozone-air mixture or air only through a diffuser plate at the bottom of the reactor. The injection of the gas increases the reactor headspace pressure until the designated pressure (e.g. 1034 kPa) is achieved. Once the desired pressure is reached, the inlet valve is closed and the mixture is stirred and allowed to equilibrate until a specified duration of time (e.g. 30 seconds) has passed from the start of the compression/injection. After the designated period of time has passed, the pressure is released by venting the gas in the reactor headspace. Decompression was carried out at controlled rates of between 3 seconds and 150 seconds for venting. The compression/decompression cycles were repeated a total of ten times (or as otherwise specified). Similar to the images shown in FIG. 1, the samples prior to treatment showed an abundance of filamentous bacteria and flocs with discernible rotifer present. After treatment the samples showed little biomass remaining but rather disperse nondescript flocs and viscous patches of liquid in water. Disintegration of the activated sludge seemed to occur within 11 minutes during 10 pressure cycles.

Figure 4:
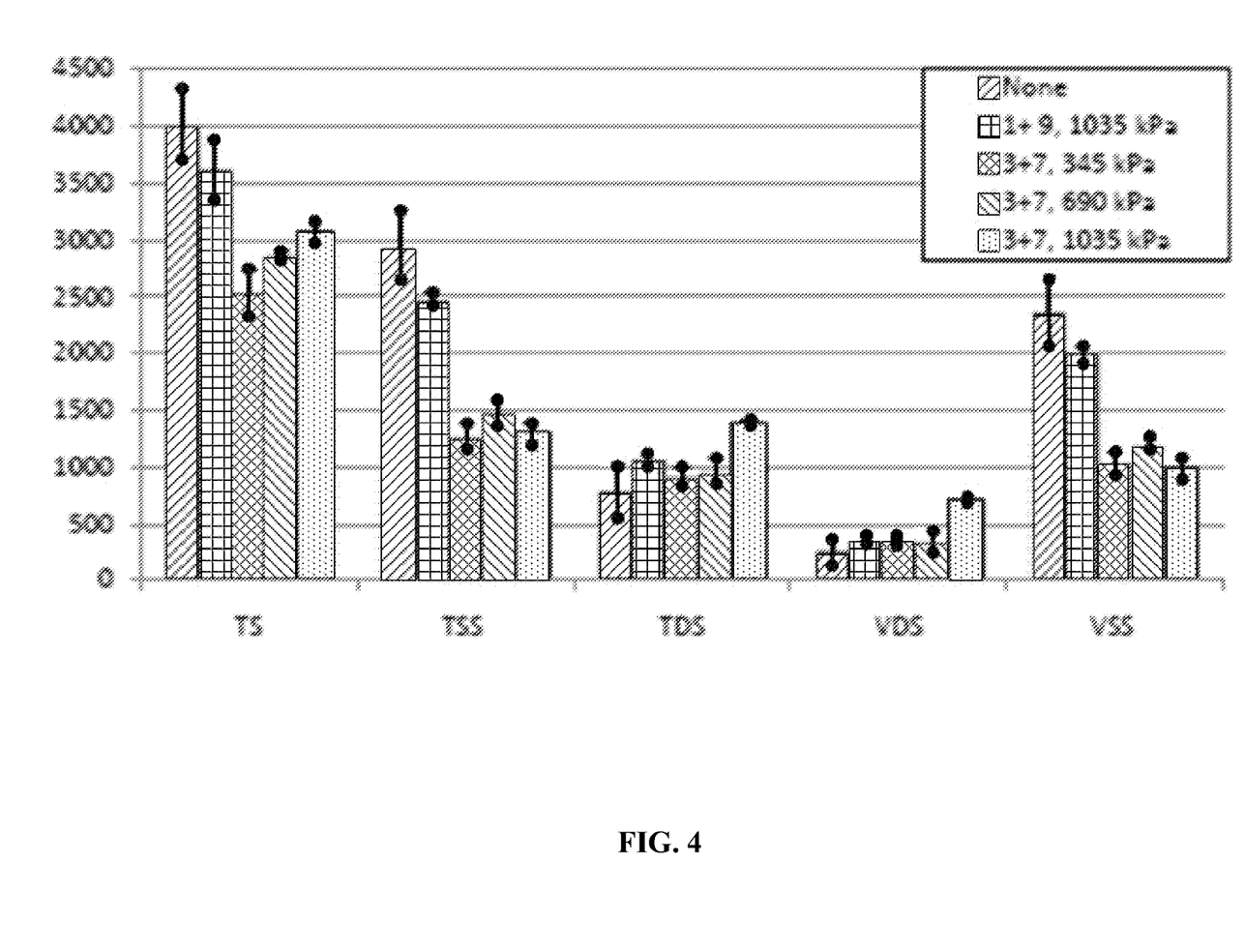
FIG. 4 is a plot of the solid characteristics of untreated and treated activated sludge at various pressures and ozonation plus aeration cycles.

FIG. 4 shows the fractions of various solids in the activated sludge after the various treatment profiles of 1) 1 ozonation+9 aeration at 1035 kPa; 2) 3 ozonation cycles and 7 aeration at 345 kPa; 3) 3 ozonation+7 aeration at 690 kPa; and 3 ozonation and 7 aeration at 1035 kPa. Total solids in the samples decreased 10-37%. Loss of the total solids after ozonation is often observed and attributed to mineralization by the ozone. However, loss of the total solids solely via mineralization by ozone is untenable in this case. Activated sludge is widely represented as $C_5H_7NO_2$ and, for each gram of the activated sludge mineralized, 1.42 g of $O_2$ or ozone is required. Based on the headspace volume of 1.2 L that was charged to 1000 kPa with $O_3$/air mixture (0.06% $O_3$) at the initial 3 cycles, the amount of $O_3$ brought into the reactor would be 43 mg and, even when completely used up, could only account for about 30 mg of mineralized activated sludge. This would not account for the loss of 100-370 mg of activated sludge loss observed in the 300 mL of suspension that was treated. Without being limited by theory, it is believed that the total solids loss in the treated suspension was likely due in part to a portion of the cell water content being homogeneously incorporated into the bulk water phase when the microbes were ruptured. Whereas the cell water content was part of the total solids in the untreated activated sludge, the ruptured cells were no longer measured as total solids after their rupture in the compression cycles.

Figure 3:
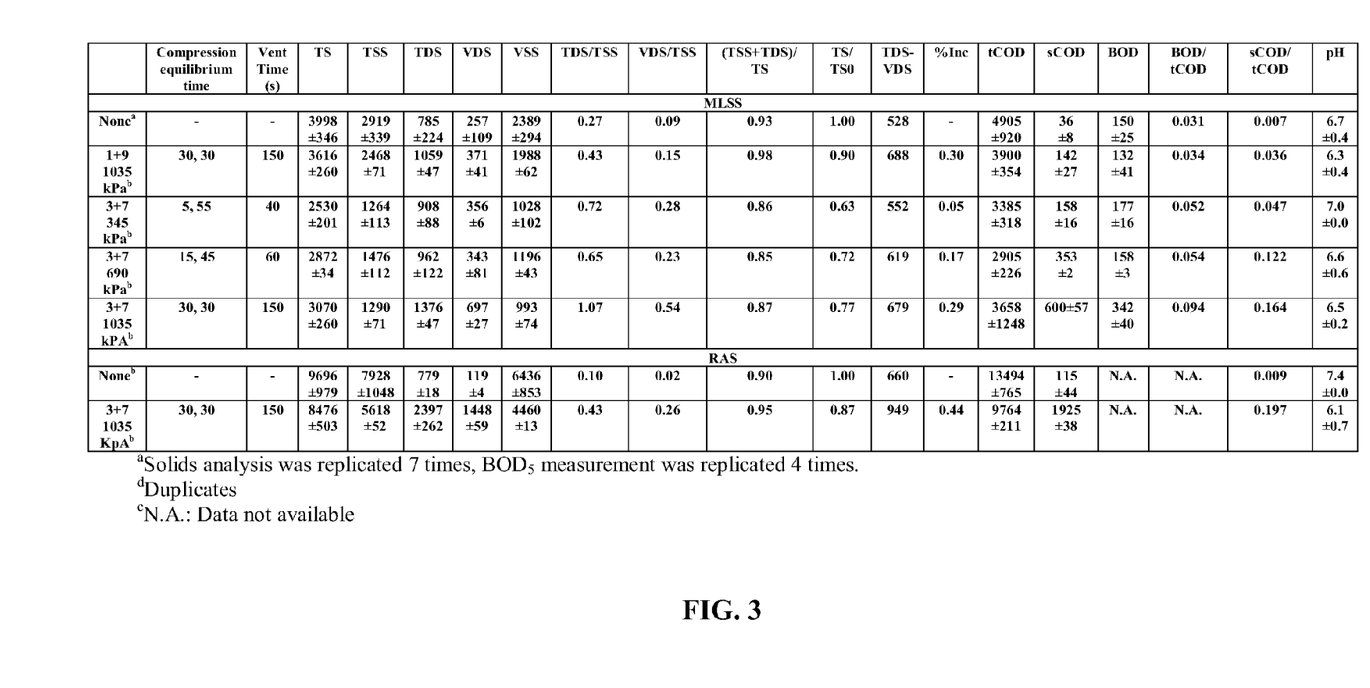
FIG. 3 shows various characteristic measures of the treated and untreated activated sludge.

When multiple ozonation cycles were used, the TSS underwent significant reduction, dropping to about half of its untreated state. FIG. 3 shows various measured characteristics of the treated activated sludge samples. It is noted that an increasing TDS/TSS ratio of the activated sludge after treatment is indicative of solubilization. The VDS content reflects the amount solubilized cell substances after rupture. It is noteworthy that the measured TSS plus the measured TDS agreed well with the measured total solids within about 15%. This indicates good mass balance.

FIG. 3 also shows the tCOD, sCOD, and BOD measured for the activated sludge before and after treatment. The ratio of the BOD/tCOD can be representative of the biodegradability of the substrate, with the fraction being close to unity representing a readily biodegradable substrate. As indicated in FIG. 3, the BOD/tCOD ratio increases by 3 fold from 0.031 to 0.094, indicating increased substrate utilization rate after 3 ozonation and 7 aeration cycles at 1000 kPa. Similarly, the sCOD/tCOD ration indicates the relative amount of soluble contents that can be utilized and this ratio increases from 0.0075 to 0.16, a 21 fold increase.

In an effort to confirm cell rupture and release of cellular contents, testing was performed to identify the presence of DNA and protein and to quantify these substances in the activated sludge suspensions both before and after treatment. Gel electrophoresis results showed a complete absence of DNA before treatment with significant DNA smears on the gel after treatment. Additional quantifications of DNA and proteins were performed using colorimetrix agents diphenylamine and Coomasie Blue G-250. The results of the tests are shown in the Table 1.

TABLE 1

| Treatment | No Treatment | 3 ozonation plus 7 Aeration |
|---|---|---|
| DNA (mg/L) | 6 ± 3 | 35 ± 3 |
| Protein (mg/L) | Not present | 41 ± 4 |

As shown in Table 1, the untreated samples had concentrations of about 6 mg/L of DNA prior to treatment, which increased to about 35 mg/L DNA subsequent to treatment. Similarly, the significant amounts of protein were released following treatment. Both the increase in the levels of protein and DNA indicate rupturing of the cells.

Thus, while the present invention has been described above with particularity and detail in connection with what is presently deemed to be the most practical and preferred embodiments of the invention, it will be apparent to those of ordinary skill in the art that numerous modifications, including, but not limited to, variations in materials, temperature, function, order, and manner of operation may be made without departing from the principles and concepts set forth herein.

What is claimed is:

1. A method of deactivating biomass, comprising:
   a) performing a disrupting stage by injecting an oxidizer agent into the biomass causing disruption of cellular membranes of cells in the biomass;
   b) performing a rupture stage comprising:
      i) an injecting step comprising injecting a rupture gas into the biomass sufficient to pressurize the biomass to a first elevated pressure, wherein the rupture gas is compositionally different than the oxidizer agent;
      ii) a depressurizing step comprising depressurizing the biomass; and
      iii) repeating the injecting step and the depressurizing step of the rupture stage at least 3 times to rupture cell membranes and expose residual cell contents; and
   c) digesting the residual cell contents to form a biofuel.

2. The method of claim 1, wherein the disrupting stage further includes pressure cycling by injecting the oxidizer agent into the biomass sufficient to pressurize the biomass to a second elevated pressure and then depressurizing the biomass.

3. The method of claim 2, wherein the pressure cycling is repeated 1 to 4 times.

4. The method of claim 1, wherein the oxidizing agent is an oxidizer gas selected from the group consisting of ozone, chlorine, and mixtures thereof.

5. The method of claim 4, wherein the oxidizer gas includes ozone.

6. The method of claim 1, wherein the oxidizing agent is a liquid or a solid.

7. The method of claim 6, wherein the oxidizing agent is $KMnO_4$, $NaClO$, $K_2FeO_4$, liquid chlorine, or a mixture thereof.

8. The method of claim 2, wherein the second elevated pressure is 0-30 psi and the first elevated pressure is at least 30 psi.

9. The method of claim 2, wherein each of the first elevated pressure and the second elevated pressure is about 80 psi to about 200 psi.

10. The method of claim 2, wherein the first elevated pressure is different from the second elevated pressure.

11. The method of claim 2, wherein the injecting and depressurizing steps of the disrupting stage are performed 1 to 4 times.

12. The method of claim 1, wherein the injecting and depressurizing steps of the rupturing stage are performed 4 to 15 times.

13. The method of claim 1, wherein the injecting and depressurizing steps of the rupturing stage are performed 6 to 10 times.

14. The method of claim 1, wherein the depressurizing step of the rupture stage produces a pressure reduction of at least 50 psi in the biomass from the first pressure at the injecting step.

15. The method of claim 1, wherein the rupture gas is selected from the group consisting of air, carbon dioxide, nitrogen, argon, helium, oxygen, and mixtures thereof.

16. The method of claim 1, wherein the depressurizing leaves the biomass at ambient pressure.

17. The method of claim 1, wherein the biomass is agitated by at least one of stirring, shaking, and ultrasound during at least one of the injecting step and the depressurizing step.

18. The method of claim 1, wherein the method occurs in a reactor vessel and the injecting step and depressurizing step have a time duration of 20 seconds to 20 minutes for each step during each complete cycle.

19. The method of claim 1, wherein process takes place in a reactor that has an occupied volume to headspace volume ratio of 1:9 to about 9:1.

20. The method of claim 1, wherein the biofuel includes methane, carbon monoxide, and hydrogen.

21. The method of claim 1, wherein the biomass is activated sludge or algae.

22. The method of claim 1, wherein the steps of injecting and depressurizing have a collective duration of 20 seconds to 2 minutes.

23. The method of claim 1, wherein the steps of injecting and depressurizing have a collective duration of a duration of about 25 seconds to about 90 seconds.

24. The method of claim 1, further comprising a step of equilibrating the biomass after the pressurizing step for a period of about 10 seconds to about 90 seconds.

* * * * *